(12) United States Patent
Lendlein et al.

(10) Patent No.: US 7,037,984 B2
(45) Date of Patent: May 2, 2006

(54) INTERPENETRATING NETWORKS

(75) Inventors: Andreas Lendlein, Berlin (DE); Annette Schmidt, Neuss (DE)

(73) Assignee: mnemoScience GmbH, Aachen (DE)

( * ) Notice: Subject to any disclaimer, the term of this patent is extended or adjusted under 35 U.S.C. 154(b) by 173 days.

(21) Appl. No.: 10/418,885

(22) Filed: Apr. 17, 2003

(65) Prior Publication Data

US 2004/0024143 A1    Feb. 5, 2004

(30) Foreign Application Priority Data

Apr. 18, 2002   (DE)   ................ 102 17 351

(51) Int. Cl.
*C08L 75/06*    (2006.01)
*C08L 67/02*    (2006.01)

(52) U.S. Cl. ............... 525/454; 525/437; 525/439; 525/440; 525/451; 525/453; 525/455

(58) Field of Classification Search ........... 525/437, 525/439, 440, 451, 453, 454, 455
See application file for complete search history.

(56) References Cited

U.S. PATENT DOCUMENTS

| | | | |
|---|---|---|---|
| 3,894,075 A | | 7/1975 | Schoen |
| 4,035,548 A | | 7/1977 | Chang et al. |
| 4,085,092 A | | 4/1978 | Chang et al. |
| 4,857,579 A | * | 8/1989 | Domeier ............ 524/507 |
| 4,923,934 A | * | 5/1990 | Werner ............ 525/528 |
| 5,098,776 A | | 3/1992 | Kobayashi et al. |
| 5,155,199 A | | 10/1992 | Hayashi et al. |
| 5,442,037 A | | 8/1995 | Lee et al. |
| 6,156,842 A | | 12/2000 | Hoenig et al. |
| 6,160,084 A | | 12/2000 | Langer et al. |
| 6,479,222 B1 | * | 11/2002 | Jones et al. ........ 430/350 |
| 6,852,825 B1 | | 2/2005 | Lendlein et al. |

FOREIGN PATENT DOCUMENTS

| | | |
|---|---|---|
| DE | 689 07 553 T2 | 5/1990 |
| DE | 689 08 081 T2 | 5/1990 |
| DE | 694 26 882 T2 | 4/1996 |
| EP | 0 422 693 A2 | 4/1991 |
| WO | WO 99/42147 | 8/1999 |
| WO | WO 99/42528 | 8/1999 |
| WO | WO 99/42528 A3 | 8/1999 |
| WO | WO 01/91822 A1 | 12/2001 |
| WO | WO03/084489 A1 | 10/2003 |
| WO | WO 03/084490 A1 | 10/2003 |
| WO | WO 03/084491 A1 | 10/2003 |

OTHER PUBLICATIONS

Kim, B.K. et al. (1996) "Polyurethanes having shape memory effects," Polymer 37/26:5781-5793.
Lendlein, A. et al. (2001) "AB-Polymer Networks Based On Oligo(epsilon-Caprolactone) Segments Showing Shape-memory Properties," Proc. Natl. Acad. Sci. USA, 98/3:842-847, XP002251532.
Lendlein, A. et al. (2002) "Formgedächtnispolymere," Angewandte Chemie, 114/12:2138-2162 (Jun. 17, 2002). XP002251533.
Database WPI, Section Ch, Week 199214, Derwent Publications Lt., London, GB; AN 1992-109202 XP002251534 & JP 04 050234 A (Asahi Chem Ind Co Ltd), Feb. 19, 1992.
Patent Abstracts of Japan, vol. 016, No. 213 (C-0942, May 20, 1992 & JP 04 0457416 A (Noevir Co Ltd; Others: 01), Feb. 12, 1992.

* cited by examiner

*Primary Examiner*—Jeffrey B. Robertson
(74) *Attorney, Agent, or Firm*—Kalow & Springut LLP

(57) ABSTRACT

The present invention relates to the penetrating networks comprising a covalently crosslinked polymer component and a polyester urethane component. The materials in accordance with the present invention are suitable in particular as materials for medicinal purposes, as implants, for target controlled stimuli-sensitive drug release, as ligament augmentation and as replacement material for inter-vertebrae disks.

12 Claims, 3 Drawing Sheets

INTERPENETRATING NETWORKS

FIELD OF INVENTION

The present invention relates to the penetrating networks comprising a covalently crosslinked polymer component and a polyester urethane component.

BACKGROUND OF INVENTION

Polymeric materials are important materials in a variety of applications, in which the classic materials such as metals, ceramic and wood are no longer sufficient due to their restricted physical properties. Polymeric materials have therefore achieved a broad variety of applications not least due to the fact that the properties may be modified by varying the monomeric units. A particularly fascinating class of polymeric materials developed in recent years are the so-called shape memory polymers (in the following named "shape-memory polymers, SMP or SMP-materials"), i.e. polymeric materials which may remember one or even a plurality of shapes in memory, whereby selected changes in shape may be initiated by external stimuli, such as a change in temperature Such materials are, for example, described in the Intentional Patent Applications WO-A-99-42528 and WO-A-99-42147. A drawback of the thermoplastic materials described there is however that after a repetition of several cycles of shape amendments no exact recovery of the initial shape is achieved. Furthermore, these materials known from the prior art do show, due to irreversible creep processes during repeated shape amendments, a certain "wearout", so that desired physical properties are lost in the course of several cycles.

It is therefore the object of the present invention to provide polymeric materials overcoming the drawbacks of the prior art. The polymeric materials in accordance with the present invention furthermore should enable the possibility that by simple variation of the composition a regulation of the properties is enabled whereby materials having a desired profile of properties can be obtained.

SUMMARY OF INVENTION

The present invention solves this problem by providing the interpenetrating network in accordance with the claims. Preferred embodiments are defined in the subclaims. Furthermore, the present invention provides a process for the manufacture of the interpenetrating network in accordance with the present invention as defined in the claims. Preferred embodiments are again defined in the subclaims.

DETAILED DESCRIPTION OF THE INVENTION

Figure 1:
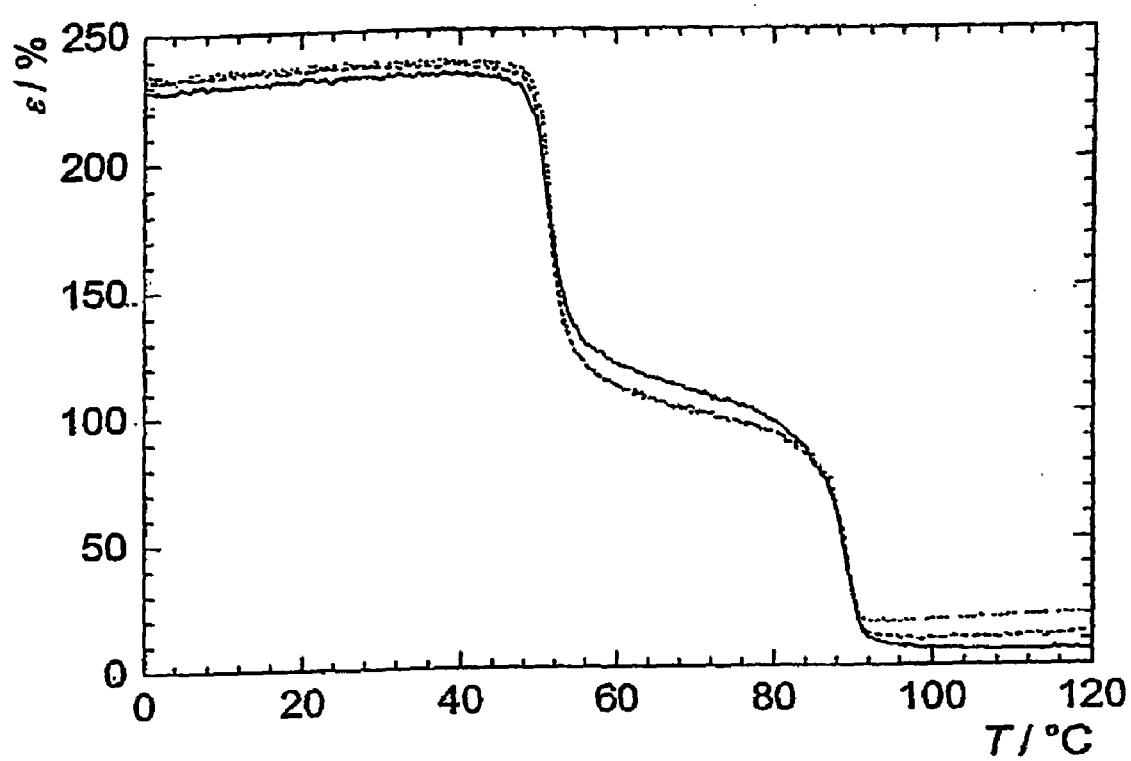
FIG. 1 shows stress-strain measurements using a network in accordance with the present invention (Example 9), illustrating course of elongation ϵ depending from temperature T during the heating of the cyclic thermo-mechanical experiment regarding a two stepped shape memory effect.

In the following the present invention is described in detail.

The interpenetrating networks in accordance with the present invention do comprise covalently crosslinked polymers which are interpenetrated by a distinct additional polymeric component. This additional polymeric component cannot be separated from the network by physical methods. However, this additional component is itself not crosslinked, neither with molecules of the own nature nor with the crosslinked component. The two essential polymeric components in accordance with the network of the present invention are described in the following.

1. Covalently Crosslinked Component

The network in accordance with the present invention comprises a polymeric component which does not show physical interaction only but which is present in a covalently crosslinked form.

This component may be preferably obtained by crosslinking functionalised macromonomers. The functionlisation enables preferably a covalent bonding of the macromonomers by reactions which do not give rise to side products. Preferably the functionlisation is provided by ethylenically unsaturated units, in particular acrylate groups and methacrylate groups, wherein the latter are preferred in particular. The macromonomers are preferably polyester macro monomers, in particular polyester macromonomers on the basis of caprolactone. Other possible polyester macromonomers are based on lactide units, glycolide units, p-dioxane units and their mixtures and mixtures with caprolactone units. However, polyester macromonomers comprising caprolactone units are in particular preferred.

When crosslinking the above described macromonomers networks having a uniform structure are obtained if only one type of macromonomer is used. Employing two types of macromonomers gives rise to networks of the type AB. Such networks of the type AB may also be obtained if functionalised macro monomers are copolymerised with suitable low molecular weight or oligomeric compounds. In the case that the macromonomers are functionalised with acrylate groups or methacrylate groups, suitable compounds which may be copolymerised therewith are low molecular weight acrylates, methacrylates, diacrylates or dimethacrylates. Preferred compounds of this type are acrylates, such as butylacrylate or hexal acrylates and methacrylates such as methylmethacrylate and hydroxyethyl methacrylate.

These compounds which may be copolymerised with the macromonomer may be present in an amount of from 5 to 70 wt %, based on the network of macromonomer and low molecular weight compound, preferably in an amount of from 15 to 60 wt %. The introduction of varying amounts of low molecular weight compounds is achieved by adding corresponding amounts of the compound to the mixture to be crosslinked. The introduction of the low molecular weight compound into the network in accordance with the present invention is achieved in an amount corresponding to the amount added to the mixture to be crosslinked.

The macro monomers to be used in accordance with the present invention are described in detail in the following.

The macromonomers to be crosslinked covalently do show preferably a number average molecular weight, determined by a GCP analysis of from 2000 to 30,000 g/mol, preferably of from 5000 to 20,000 g/mol and in particular preferably from 7500 to 15,000 g/mol. The macromonomers to be crosslinked covalently preferably do show at both terminals of the macromonomer chain a methacrylate group. Such a functionalisation enables the crosslinking of the macromonomers using simple photo initiation (irradiation).

The macromonomers to be used in accordance with the present invention are preferably polyesters, comprising crosslinkable end groups. A polyester which is in particular preferred in the present invention is a polyester on the basis of caprolactone, for which the above given information regarding the molecular weight holds true. The preparation of such a polyester macromonomer, functionalised at the terminals, preferably with methacrylate groups, may be achieved by simple synthesis which are known to the skilled person. These networks, without taking into account the further essential polymeric component of the present invention, do show semi-crystalline properties and do show a melting point of the polyester component (as determined by DSC measurements) which may be controlled owing to the type of the used polyester component. However, generally this temperature (Tm1) is in the vicinity of 50° C.

2. Component Which is Not Covalently Crosslinked

The interpenetrating network in accordance with the present invention furthermore comprises a component made from polyester urethanes. These polyester urethanes are present in the network in accordance with the present invention in a not covalently crosslinked form but do show, between differing sections of the polyester urethanes physical interactions at most.

The polyester urethane present in the penetrating network in accordance with the present invention comprises preferably, as ester component, units derived from caprolactone and/or pentadecalactone. Particularly preferred polyester urethanes are those which do comprise, in addition to units from caprolactone, also units from pentadecalactone. Other possible ester components are units on the basis of p-dioxanone and other compounds forming ester segments, which are known for shape-memory materials and which have been listed above in connection with the macro monomers. Preferred however are, in the context of the present invention, the polyester urethanes showing as ester components units derived from caprolactone and/or pentadecalactone, in particular preferred units of caprolactone and of pentadecalactone.

The ester component of the polyester urethane preferably shows a number average of the molecular weight of from 1000 to 20,000, preferably from 1500 to 15,000 g/mol, determined by GPC. The ester component may be present in the form of homopolyester blocks or in the form of copolyester blocks, preferred however are homopolyester blocks. When caprolactone units and pentadecalactone units are present together in the polyester urethane used in accordance with the present invention it is preferred in accordance with the above given statement, that the caprolactone units and the pentadecalactone units, respectively, are present as homopolyester blocks (sometimes in the following also called "segments") in the polyester urethane.

In a further preferred embodiment polypentadecalactone segments are used in a polyester urethane. These preferred embodiments in accordance with the present invention do employ the polypentadecalactone segments as hard segment in the polyester urethanes which, in addition to the polypentadecalactone segments do comprise further polyester segments, preferably polycaprolactone segments, which serve as soft segments.

The polypentadecalactone segment, contained in the polyester urethane used in accordance with the present invention, is usually introduced into the polyester urethane In the form of a macro diol. This segment may be obtained by ring opening polymerisation from ω-pentadecalactone employing tin catalysis and using ethylene diol as initiator. The ratio of initiator to monomer controls the molecular weight of the segment. The molecular weight of the polypentadecalactone segments in the polyester urethane used in accordance with the present invention is not critical. Usually the number average of the molecular weight is however in the range of from 1000 to 20,000 g/mol, preferably to 2000 to 11,000 g/mol, determined by GPC-analysis. The macro diol from pentadecalactone may be converted to a polyester urethane using those diisocyanates which are typically employed for the preparation of polyurethanes. Preferred diisocyanate are compounds having the formula O=C=N—R—N=C=O wherein R is aromatic or aliphatic. Preferably however R is aliphatic comprising a carbon chain of from 1 to 10, preferably 2 to 8 and in particular preferably 4 to 7 carbon atoms. This carbon chain may be saturated with hydrogen or may show additional substituents. These substituents comprise short chain alkyl groups, in particular methyl groups. A preferred diisocyanate is trimethyl hexane-1,6-diisocyanate.

By varying the molecular weight of the polypentadecalactone segment the properties of the polyester urethane may be varied. The molecular weight of the polyester urethane is not critical and may be selected in accordance with the desired use. Typical molecular weights (number average, determined by GPC) are in the range of from 100,000 to 250,000 g/mol, preferably within the range of 150,000 to 200.000 g/mol.

The statements given above are also valid for polyester urethanes which comprise as ester component polycaprolactone segments.

Preferably the polyester urethane, if a polypentadecalactone segment is present, does comprise at least one further segment, wherein this additional segment may be selected among different chemical components, such as partially crystalline segments, comprising polyester segments, polyether ester segments and polyether segments, such as polycaprolactone segments (PCL), polycaprolactone-co-polytetrahydrofurane segments (PCL-co-pTHF), tetrahydrofurane segments (pTHF), polypropyleneglycol segments (PPG) and polyethyleneglycol segments (PEG), as well as glassy segments, comprising polyester and copolyester, such as poly-L-lactid-co-glycolide (ran) (PLGA) and poly-DL-lactide (P-DL-LA), in particular preferred a polycaprolactone segment. These polyester urethanes are block copolymers with polypentadecalactone segments, bonded to other segments, preferable polycaprolactone segments. The further segments, preferable the polycaprolactone segment may, as described above for the polypentadecalactone segment, be introduced into the polyester urethane in accordance with the present invention in the form of a macro diol. Those macro diols may for example be obtained by ring opening polymerization of ε-caprolactone, in accordance with the processes described above.

The molecular weight of the additional segments, as described above for the polycaprolactone segments, is not critical. However, typically these segments do show a number average of the molecular weight, determined by GPC, of from 1000 to 20,000 g/mol preferably 2,00 to 11,000 g/mol, wherein the preferred range for the PEG segments is from 2000 to 20,000 g/mol, for the PLGA segments from 4000 to 9000 g/mol and for P-DL-LA from 5000 to 11,000 g/mol. The polyester urethanes comprising additional segments, preferably polycaprolactone segments do show preferably a molecular weight of from 50,000 to 250,000 g/mol (number average, determined by GPC), more preferably of from 60,000 to 200,000 g/mol and in particular preferably from 62000 to 196,000 g/mol (and in some embodiments of from 55,000 to 100,000 g/mol). The content of polypentadecalactone units may be varied over a broad range, preferably the content of pentadecalactone units is in the range of from 10 to 80 wt % in particularly within the range of from 20 to 60 wt %.

For the in particular preferred embodiment it can be stated that the molecular weight of the polycaprolactone segment is not critical. Typically however this segment does show a number average of the molecular weight, determined by GPC of from 1000 to 20,000 g/mol, preferably of from 2000 to 11,000 g/mol. The polyester urethanes comprising polycaprolactone segments do show preferably a molecular weight of from 100,000 to 250,000 g/mol (number average, determined by GPC) more preferably from 120,000 to 190,000 g/mol. The content of pentadecalactone units may vary over a broad range but preferably the content of pentadecalactone units is within the range of from 10 to 80 wt %, in particular within the range from 20 to 60 wt %.

Satisfactory interpenetrating networks in accordance with the present invention may be prepared with the following polyester urethanes:

Polypentadecalactone segment: Molecular weight 1000 to 10,000 g/mol (number average), preferably 1500 to 5000, in particular 2000 to 3000 g/mol.

Polycaprolactone segment: Molecular weight 3000 to 11,000 g/mol (number average), preferably 4000 to 10,000 g/mol.

Polycaprolactone-co-polytetranadrofurane segment: molecular weight 1000 to 5000 g/mol (number average), preferably 1500 to 3500 g/mol.

Polytetrahydrofurane segment: Molecular weight 1000 to 5000 g/mol (number average), preferably 1500 to 3000 g/mol.

Polypropyleneglacol segment: molecular weight 1000 to 8000 g/mol (number average), preferably 1200 to 4500 g/mol.

Polyethyleneglycol segments; Molecular weight 1000 to 25,000 g/mol (number average), preferably 1500 to 20,0000 g/mol.

Poly-L-lactide-co-glycolide segment (ran): Molecular weight 4000 to 10,000 g/mol (number average), preferably 5000 to 8000 g/mol.

Poly-DL-lactide segment: Molecular weight 4000 to 15,000 g/mol (number average), preferably 5000 to 11,000 g/mol.

Polyesterurethane: Molecular weight 50,000 to 200,000 g/mol (number average), preferably 60,000 to 190,000 g/mol; content of the additional segment 20 to 80 wt %, preferably 45 o 70 wt %, more preferably 50 to 60 wt %, content polypentadecalactone segment 80 to 20 wt %, preferably 55 to 30 wt %, more preferably 40 to 50 wt %.

If the above-mentioned polyester segments are converted by a polyaddition reaction with the above described diisocyanates to the polyesterurethanes in accordance with the present invention, the variation of the respective contents and molecular weights of the polyester segments enables a control of the profile of properties of the resulting polyesterurethanes over a broad range. This preferred embodiment of the present invention accordingly provides a polymeric system which, by simple variation of simple starting materials, enables a controlled modification of the properties. The networks in accordance with the present invention do show, due to the possibilities of modification for the polyester urethane to be used, a plurality of variables for the modification of the properties, such as length of the segments in the polyester urethane, content of polyesterurethane within the network and chemical composition of the polyesterurethane.

The preferred polyesterurethanes in accordance with the present invention, which do comprise in addition to the polypentadecalactone segments also polycaprolactone segments do display further additional beneficial profiles of properties.

The use of a polyesterurethane comprising polycaprolactone segments enables the benefit, for the networks in accordance with the present invention, that identical segments are present in the covalently crosslinked part and in the polyesterurethane (it also the network comprises caprolactone units), which may give rise to a common crystalline phase. This co-crystallization enables a penetration, within the interpenetrating networks in accordance with the present invention, on the molecular level, so that less problems occur during the manufacture of the preferred interpenetrating networks in accordance with the present invention.

The use of polyesterurethanes having polypentadecalactone segments gives rise to further advantages for the interpenetrating networks in accordance with the present invention. Materials in accordance with the present invention which for example do comprise polycaprolactone segments, having a melting temperature of about 50° C. (see above) may be provided with a second melting temperature by introducing polypentadecalactone segments (may be determined by DSC measurements). This second temperature (Tm2) is in the vicinity of 90° C. The polycaprolactone segments and the polypentadecalactone segments further do not form mixed crystals but are present as distinct phases.

Furthermore, the mechanical properties may be varied in a controlled manner over a broad range. With increasing content of polypentadecalactone the value for E-module of the polyesterurethane may be increases as well. The value for the elongation at break can be controlled in a range of 600 to 1200% with increasing content of polypentadecalactone. At the same time the tensile strength may be adjusted within a range of from 4 to 10 Mpa (all values determined at 70° C.) with increasing content of polypentadecalactone segments. The decreased, i.e. slower biodegradability of the polypentadecalactone segments, compared for example with polyparadioxanone segments, may furthermore enable that the preferred polyesterurethanes in accordance with the present invention are employed in applications for which the polyesterurethanes having polyparadioxane segments may not be employed due to the fast degradation and the unsatisfactory stability associated therewith. Compared with polyesterurethanes having polycaprolactone segments and polyparadioxanone segments the preferred polyesterurethanes in accordance with the present invention furthermore do display an increased stability during production and granulation, so that the manufacture and processing of the networks in accordance with the present invention is simplified.

Examinations have shown that an increase of the content of polyesterurethane within the networks in accordance with the present invention does give rise to an increase of the elongation at break, at 22° C. for example of from 250 to 450%. At the same time the difference between yield point and tensile strength increases.

Particularly preferred polyesterurethanes, used in the present invention, which show polypentadecalactone segments as well as polycaprolactone segments furthermore display shape-memory properties, so that these preferred materials themselves may be described as shape-memory polymers (SMP).

The interpenetrating networks in accordance with the present invention are obtained by crosslinking terminally functionalised macromonomers in the presence of the polyesterurethanes. In addition to the macromonomers, as described above, low molecular weight comonomers, such as acrylates or methacrylates, for example alkylacrylates or alkylmethacrylates may be employed, so that covalently crosslinked AB-networks are produced. Crosslinking may be achieved by irradiating a mixture, comprising the polyester urethane component and the terminally functionalised macromonomer component and optionally a low molecular weight comonomer. Suitable process parameters are the irradiation of a mixture in the form of a melt with light having a wavelength of preferably 380 nm. The mixture to be crosslinked is preferably obtained, prior to melting and crosslinking, by dissolving the starting materials to be used in a suitable solvent and precipitating the mixture from the solution in a precipitant. Preferred solvents are inert, polar solvents, in particular chloroform. The solution to be produced preferably shows a solid concentration of from 2 to 20 wt %, preferably 8 to 12 wt %.

Precipitation preferably occurs by dropping the solution drop wise into a suitable, inert, unpolar precipitant, preferably an aliphatic hydrocarbon precipitant, in particular preferably a fraction of hexanes. Precipitation occurs quantitatively so that the desired mixture of polyester urethane component and functionalised macro monomer component may be produced with the preparation of the solution. Prior to the conversion into the melt the precipitated mixture is preferably dried, in particular using relatively mild conditions of from 25 to 40° C. and ambient pressure.

Crosslinking, which may be carried out as described above, yields an interpenetrating networks comprising covalently linked macro monomer components, and dispersed therein the not covalently linked polyester urethane. These polyester urethanes however may give rise to regions showing physical interaction, which may be formed by the polyester segments of the polyester urethane, which may be present in crystalline form.

The interpenetrating network in accordance with the present invention may show varying amounts of the different components.

Suitable amounts of terminally functionalised macromonomer components are in the range of from 5 to 99 wt %, based on the mixture of macromonomer component and polyesterurethane component, preferably from 40 to 95% and more preferably from 60 to 90 wt %.

The polyester urethane component usually is present in an amount of from 1 to 95 wt %, preferably of from 5 to 60 wt %, more preferably of 10 to 40 wt %, based on the mixture of macro monomer component and polyesterurethane component.

The polyesterurethane component preferably comprises polyesterurethanes on the basis of caprolactone and/or pentadecalactone. The total amount, within the interpenetrating network in accordance with the present invention, of pentadecalactone preferably is within the range of from 2 to 30 wt %, more preferably from 6 to 25 wt %, based on the mixture of macro monomer component and polyesterurethane component.

The interpenetrating networks in accordance with the present invention do show the following properties.

The interpenetrating networks in accordance with the present invention are good SMP materials having high recovery values, i.e. the initial shape will be recovered to a high degree, even after a plurality of cycles of shape amendments. This degree usually is above 90%. Furthermore a loss of mechanical properties is not observed. The interpenetrating networks in accordance with the present invention comprising polyesterurethanes on the basis of caprolactone do show a melting point (transfer point), in association with a shape amendment point. The networks comprising polyesterurethanes on the basis of caprolactone and pentadecalactone do show two such melting points, so that these preferred materials in accordance with the present invention may remember two different shapes in memory. The shape-memory properties of the materials in accordance with the present invention are defined in the following.

Shape-memory polymers in accordance with the present invention are materials which, due to their chemical/physical structure, are able to conduct controlled amendments of the shape. In addition to their original permanent shape the materials comprise an additional shape which may be formed with the material temporarily. Such materials are characterized by two features. Thee materials do comprise so-called trigger segments which may initiate a transfer (shape amendment) which may be initiated with an external stimulus, usually a change in temperature. In addition these materials do comprise covalent crosslinking points which are responsible for the so-called permanent shape. This permanent shape is defined by the three-dimensional structure of a network. The crosslinking points present within the networks in accordance with the present invention are of covalent nature and are obtained in the preferred embodiments of the present invention by polymerising the terminal methacrylate groups. The trigger segments, which initiate the thermally induced transfer (shape amendment), are, in relation to the preferred embodiments, the polycaprolactone segments and the polypentadecalactone segments, respectively, which, due to their crystalline or non-crystalline structure, initiate an amendment of the shape. The thermal transfer point is defined by the melting temperatures of the crystalline regions Tm. Above Tm the material is amorphous and elastic. If a sample is accordingly heated to above the transfer Tm and if this material is then deformed in its flexible state and if this deformed material is then cooled before the transfer temperature the chain segments are fixed due to a freezing of degrees of variance within the deformed shape (programming). Temporary crosslinking points (non-covalent) are formed so that the sample, without external stimulus, cannot recover the original shape. Heating the sample again to a temperature above the transfer temperature releases the temporary crosslinking points and the sample recovers the original shape. A repetition of the programming step may recover the temporary shape The precision which the original shape is recovered is called recovery ration. The interpenetrating networks in accordance with the present invention which do show two transfer temperatures Tm (i.e. the preferred systems comprising caprolactone segments and pentadecalactone segments), may be processed in accordance with the above given description so that two temporary shapes are programmed one after the other. The first, permanent shape is fixed as defined above due to the covalent crosslinking points. The second, temporary shape is programmed by deforming the material above the upper transfer temperature Tm2 and subsequently cooling. The fixation of this form is achieved with crystalline crosslinking points of the pentadecalactone segments. The third shape which is again a temporary shape is determined by the lower transfer temperature Tm1 (programming is achieved by deforming above this temperature and subsequently cooling) The fixation of this shape is achieved with the crystalline crosslinking points of the caprolactone segments. Suitable stress-strain-experiments are able to display the shape memory effect. An example of such a stress-strain-measurement is shown in FIG. 1 The material evaluated there, an interpenetrating network having covalently crosslinked polycaprolactone segments and a polyesterurethane component on the basis of caprolactone and pentadecalactone, does show two changes in shape which are displayed in the diagram in the form of two steps. The fact that the three repetitions of the measurement do show very similar results (small variation of the obtained data) does show that the material furthermore provides a very good recovery ratio, as well as a good retention of the shape memory effect.

The interpenetrating networks in accordance with the present invention may comprise, in addition to the above discussed essential components, further materials, as long as the function of networks is not affected. Such additional materials may be colorants, fillers or additional polymeric materials, which may be used for various purposes. In particular for medicinal applications the interpenetrating networks in accordance with the present invention may comprise medicaments and diagnostic agents, such as contrast increasing agents. The materials in accordance with the present invention are suitable in particular as materials for medicinal purposes, as implants, for the target controlled stimuli-sensitive drug release, as ligament augmentation and as replacement material for inter-vertebrae disks.

EXAMPLES

The following examples further illustrate the present invention.

Preparation of Interpenetrating Networks

Networks are obtained by irradiating molten mixtures with UV light having a wavelength of 308 nm. The mixtures comprised a dimethacrylate polycaprolactone (DMPC) (Mn=10,000 g/mol), obtained by ring opening polycondensation of caprolactone and subsequent conversion of the terminal groups, so that both terminals were provided with methacrylate groups. Additionally the mixtures in each case did comprise a polyester urethane (PU) of different nature (i.e. showing a differing content of pentadecalactone (PDL)), as described in the following Table. Mixtures were obtained by dissolving the respective components in chloroform in order to prepare a solution having a concentration of 10 wt %. Subsequently these solutions were transferred drop wise into a fraction of hexanes, in order to precipitate the starting materials in the desired mixture. Mixtures were dried at 35° C. until no further change in weight was detected and then melted at 120° C. The polyesterurethanes were obtained by ring-opening polymerisation of caprolactone and pentadecalactone, respectively, and coupling the obtained blocks, showing terminal diol groups by using isocyanates. The blocs did show a number average of the molecular weight of 10,000 g/mol.

The shape in which cross-linking is carried out corresponds to the permanent shape.

| No. | Wt.-% DMPC | Wt.-% PU | Mn PU (g/mol) | Wt.-% PDL within the network | Tg (° C.) |
|---|---|---|---|---|---|
| 1 | 90 | 10 | 176000 | 6 | −62 |
| 2 | 80 | 20 | 176000 | 9 | −64 |
| 3 | 70 | 30 | 176000 | 13 | −69 |
| 4 | 60 | 40 | 176000 | 18 | −67 |

-continued

| No. | Wt.-% DMPC | Wt.-% PU | Mn PU (g/mol) | Wt.-% PDL within the network | Tg (° C.) |
|---|---|---|---|---|---|
| 5 | 50 | 50 | 176000 | | |
| 6 | 70 | 30 | 170000 | 0 | −64 |
| 7 | 70 | 30 | 120000 | 5 | −61 |
| 8 | 70 | 30 | 196000 | 9 | −66 |
| 9 | 70 | 30 | 185000 | 22 | −69 |
| 10 | 70 | 30 | 192000 | 23 | |

The polymeric, interpenetrating networks were evaluated with respect to their thermal and mechanical properties. The results of these evaluations are summarized in the following table.

| No. | Tm1 (° C.) | Tm2 (° C.) | E-Module at 22° C. (MPa) | Elongation at break at 22° C. (%) | Recovery ratio after 5 cycles (%)* |
|---|---|---|---|---|---|
| 1 | 55 | 89 | 45 | 250 | 99 |
| 2 | 52 | 90 | 52 | 310 | 96 |
| 3 | 51 | 89 | 53 | 390 | 83 |
| 4 | 54 | 92 | 65 | 375 | 87 |
| 6 | 53 | | 56 | 425 | 98 |
| 7 | 53 | 88 | 53 | 425 | 97 |
| 8 | 53 | 89 | 62 | 445 | 93 |
| 9 | 53 | 92 | 70 | 375 | 87 |

*thermal transfer at Tm1

Figure 2:
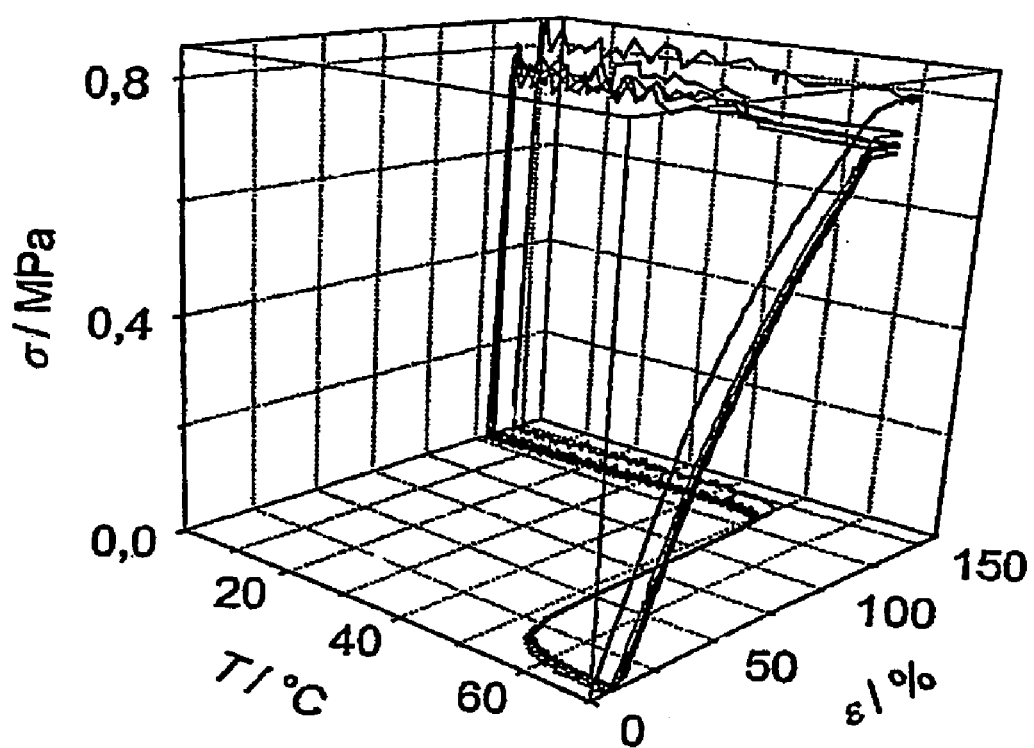
FIG. 2 shows a three-dimensional representation of temperature T, elongation ϵ and stress α during the cyclic thermo-mechanical standard experiment, in accordance with the present invention (Examples 8 and 9).

These experiments demonstrate the superior properties of the interpenetrating networks of the present invention. The networks are characterized by good values for the total recovery ratio after 5 cycles, which is representative for SMP-properties. Materials of the prior art do show often values of less than 80%. FIG. 2 displays the respective measurements for an interpenetrating network of the present invention, where the evaluation has been carried out regarding the shape memory effect at Tm1.

Figure 3:
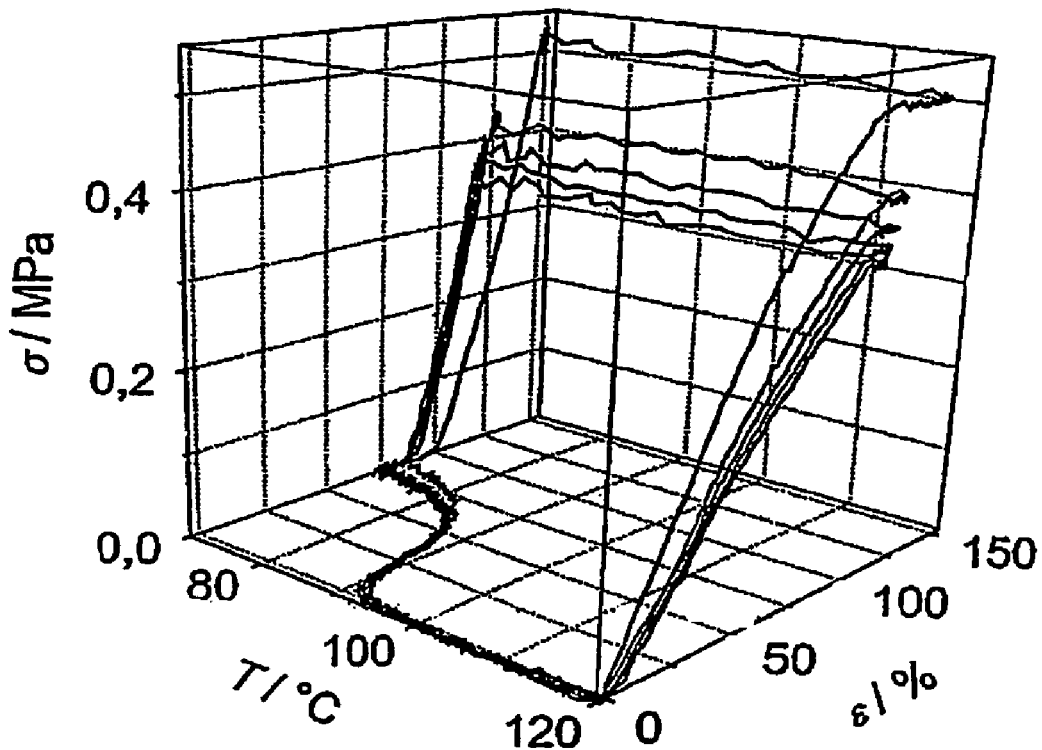
FIG. 3 shows a three-dimensional representation of temperature T, elongation ϵ and stress α durin the cyclic thermo-mechanical standard experiment between $T_h=120$ and $T_f=70°$ C. in accordance with the present invention (Examples 8 and 9).

FIG. 3 shows the corresponding data for an experiment at Tm2, where recovery ratios of >99% were obtained.

The second, higher melting temperature present in the preferred materials of the present invention enables that these materials may remember two shapes, i.e. have two shapes in memory. By simple variation of the main components of the networks of the present invention a certain simplicity of synthesis is secured. Varying the composition, as demonstrated above enables the controlled production of polymeric materials having desired properties. FIG. 1 may be referred to in this context, since this figure displays the two shape memory effects which may be triggered one after the other.

The invention claimed is:

1. An interpenetrating network comprising a polymer component that is covalently crosslinked, obtainable by crosslinking the polymer component in the presence of a polyester urethane, wherein the polyester urethane comprises at least segments derived from pentadecalactone and segments derived from partially crystalline segments that comprise polyester segments, polyether ester segments, or polyether segments, or glassy segments that comprise polyester or copolyester, and wherein the polyester urethane is not crosslinked and not covalently bonded to the polymer component.

2. Interpenetrating network according to claim 1, wherein the polymer component is a polyester.

3. Interpenetrating network according to claim 1, wherein the polymer component is terminally functionalized with methacrylate groups.

4. Interpenetrating network according to claim 1, wherein the polyester urethane comprises segments derived from polycaprolactone (PCL), polycaprolactone-co-polytetrahydrofurane segments (PCL-co-pTHF), tetrahydrofurane segments (pTHF), polypropyleneglycol segments (PPG) or polyethyleneglycol segments (PEG).

5. Interpenetrating network according to claim 1, wherein the polyester urethane comprises segments derived from copolyester is poly-L-lactid-co-glycolide (ran) (PLGA) or poly-DL-lactide (P-DL-LA).

6. Interpenetrating network according to claim 1, wherein the polyester urethane comprise segments derived from a polycaprolactone segment.

7. Interpenetrating network according to claim 1, wherein the polymer component is a dimethacrylate of a polycaprolactone.

8. Process for preparing an interpenetrating network which comprises irradiation with UV light of a melt comprising an interpenetrating network as defined in claim 1.

9. Process according to claim 8, wherein the polymer component of the network is a polyester.

10. Process according to claim 8, wherein the polymer component of the network is terminally functionalized at all terminals with methacrylate groups.

11. Process according to claim 8, wherein the polyester urethane of the network comprises segments derived from caprolactone and pentadecalactone.

12. Process according to claim 8, wherein the polymer component of the network is a dimethacrylate of a polycaprolactone.

* * * * *